(12) United States Patent
Herrlein et al.

(10) Patent No.: US 7,727,468 B2
(45) Date of Patent: Jun. 1, 2010

(54) SYSTEM FOR EVALUATING THE PH AND BUFFERING CAPACITY OF MOISTURE CONTAINING CLEANSING ARTICLES

(75) Inventors: Mathias Kurt Herrlein, Hofheim (DE); Hang Nhung Ho, Cincinnati, OH (US); Trang Le, Bad Soden am Taunus (DE); Philip Andrew Sawin, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1049 days.

(21) Appl. No.: 11/153,751

(22) Filed: Jun. 15, 2005

(65) Prior Publication Data

US 2005/0276769 A1    Dec. 15, 2005

Related U.S. Application Data

(60) Provisional application No. 60/579,867, filed on Jun. 15, 2004.

(51) Int. Cl.
   *G01N 33/00* (2006.01)
(52) U.S. Cl. .......................... 422/61; 422/56; 436/136; 510/130; 510/137; 510/138; 510/141; 510/143; 510/155; 510/156; 510/157; 510/160
(58) Field of Classification Search .................. 510/110, 510/130, 137, 138, 141, 143, 155–157, 160, 510/844–848; 424/401, 443; 422/56, 61; 436/13, 163; 514/844–848
See application file for complete search history.

(56) References Cited

U.S. PATENT DOCUMENTS

| | | | |
|---|---|---|---|
| 4,431,560 A * | 2/1984 | Lake et al. ................... | 510/100 |
| 4,908,215 A * | 3/1990 | Perlman ..................... | 424/661 |
| 4,960,585 A | 10/1990 | Tehrani et al. | |
| 5,792,384 A | 8/1998 | Warren et al. | |
| 5,823,953 A | 10/1998 | Roskin et al. | |
| 6,440,437 B1 | 8/2002 | Krzysik et al. | |
| 6,459,014 B1 * | 10/2002 | Chmielewski et al. ....... | 604/360 |
| 6,488,943 B1 * | 12/2002 | Beerse et al. ................ | 424/401 |
| 6,951,642 B2 * | 10/2005 | Scholz et al. ............. | 424/78.17 |
| 2003/0162684 A1 * | 8/2003 | Huyhn et al. ................ | 510/438 |
| 2003/0164136 A1 * | 9/2003 | Klofta et al. ................. | 116/206 |
| 2003/0185783 A1 * | 10/2003 | Terazaki ................... | 424/70.12 |

FOREIGN PATENT DOCUMENTS

| | | |
|---|---|---|
| GB | 1 313 180 A | 4/1973 |
| JP | 2002 256291 | 9/2002 |
| WO | WO 98/38905 A1 | 9/1998 |

OTHER PUBLICATIONS

Translation for JP 2002-256291, Sep. 11, 2002.*
PCT Search Report, mailed Jun. 14, 2005, 3 pages, PCT/US2005/020734.

* cited by examiner

*Primary Examiner*—Jill Warden
(74) *Attorney, Agent, or Firm*—Amy M. Foust; Matthew P. Fitzpatrick

(57) ABSTRACT

A system comprising a moisture containing cleansing article and a visual pH indicator changing color at a pH above 4.0. The system can comprise a buffer, having preferably a pKa above 5.5. The system can comprise a set of instructions for evaluating moisture containing cleansing articles. The pH buffer of the system can have a pKa value equal to or greater than the pH of the color change of the visual pH indicator. The pH of color change of the visual pH indicator can be equal to or greater than the pH of the lotion. The system can be used to evaluate the pH of moisture containing cleansing article lotions and to quantify the ability to neutralize alkalinity such as the alkalinity provided by residues of feces and urine over time on the skin of a baby.

14 Claims, No Drawings

SYSTEM FOR EVALUATING THE PH AND BUFFERING CAPACITY OF MOISTURE CONTAINING CLEANSING ARTICLES

CROSS REFERENCE TO RELATED APPLICATION

This application claims the benefit of U.S. Provisional Application No. 60/579,867 filed Jun. 15, 2004.

FIELD OF THE INVENTION

The invention relates to a system for evaluating the pH and buffering capacity on skin of a moisture containing cleansing article lotion. The system can comprise a moisture containing cleansing article, a pH indicator and a pH buffer.

BACKGROUND OF THE INVENTION

Moisture containing cleansing articles have many uses in everyday life: In the personal hygiene area, moisture containing cleansing articles are used to help cleaning the skin of babies, children or adults after bowel movements. In cosmetics moisture containing cleansing articles can be used to clean facial skin or other body parts. For example moisture containing cleansing articles can be used to remove residues of make-up.

Moisture containing cleansing articles usually comprise a substrate and a lotion that helps removing residues from the skin and protects the skin from a too stringent abrasive or irritating effect. The lotion can be water based, oil-based and/or can be an emulsion of water and hydrophobic components.

When moisture containing cleansing articles are put in contact with human skin, the lotion plays a crucial role in the protection of the skin: Mechanical protection from abrasion, hydration of the skin, deposition of a protective layer, are among the most common desired effects.

In personal hygiene and cosmetic uses, skin condition, prior to the use of the moisture containing cleansing article, can be in a deteriorated state: Residues or feces, urine and perspiration, for example, have a pH that increases over time. They unbalance the natural, slightly acid pH of the skin and render it more susceptible to rash, redness and irritation.

Lotions for moisture containing cleansing articles can therefore be also designed to help restoring the natural pH balance of the skin, to a natural pH of about 5.5. To that effect, lotions can be characterized by their pH (usually neutral or slightly acidic) and by their buffering capacity. The buffering capacity is an indication of how effective the lotion is in counteracting the increase over time of the pH of the residues of feces or urine (leading to an alkalinity of the skin environment) and to restore a natural skin pH.

It is of interest to evaluate the pH of moisture containing cleansing article lotions. In that regard, pH indicators are of many types: Sensors connected to an electronic system can provide a precise reading of pH. Classical titration by an acid is well known in the art. pH papers or pH strips are simple indicators that provide a pH reading over a defined pH range. They usually comprise a dried indicator dye applied on a substrate (paper strip or polymeric stick), that changes its color when immersed into an aqueous solution depending on the pH of the solution and thus provide a pH reading by comparison to a colored reference scale. pH paper sticks and pH measurement of body fluids are, for example, described in WO9838905A1 by James C. Caillouette. The association of feminine pads with a pH indicator is, for example, described in U.S. Pat. No. 5,823,953 by J. M. Richards and A. C. Roskin.

Moreover, it is also of interest to evaluate the buffering potential of various moisture containing cleansing article lotions. For instance some lotions can exhibit a neutral pH but have little effect on restoring the natural pH of the skin because they are ineffective in overcoming the pH increase over time of the residues of feces, urine or perspiration (leading to alkalinity of the skin environment). Some other lotions can exhibit both a neutral pH and a significant buffering potential and thus be much more efficient in restoring a natural skin pH balance. Net, measurement of pH is an indication of the effect of a lotion on skin but not sufficient to determine the efficiency of a lotion.

It is of interest to develop a simple test that would allow for the comparison of moisture containing cleansing article lotions as for their efficiency and ability to restore a natural pH of the skin. It is of interest to measure with this test, the pH of the lotion in a simple and visual way. It is of interest to measure the buffering potential of the moisture containing cleansing article lotions. It is finally of interest to develop a simple, fast, easy to use test to measure both the pH and the buffering potential of moisture containing cleansing article lotions. Such a test would be useful because it would allow users of wipe products to compare the effectiveness of the various products in helping to maintain a desirable skin pH.

SUMMARY OF THE INVENTION

A system is described that comprises a visual pH indicator and a moisture containing cleansing article with a lotion. The pH indicator changes color when pH becomes equal or greater than 4.0. The pH indicator can provide a reading of pH that is easy to use and quickly performed and allows for the comparison between various moisture containing cleansing articles. In some embodiments, the system further comprises a pH buffer that provides for a reservoir of alkalinity. The moisture containing cleansing articles can be tested as for ability to overcome the alkalinity of the pH buffer. The system thus provides a measurement of the capacity of the moisture containing cleansing article lotion to restore the natural pH of skin when the moisture containing cleansing articles are used on human skin. In some embodiments the pH indicator and the buffer salts are both provided as solid compounds on the same substrate such as a strip or stick.

The invention further relates to the use of such a system and to the process of evaluating the pH and the buffering capacity of moisture containing cleansing article lotions.

DETAILED DESCRIPTION OF THE INVENTION

Definitions: The following terms are used interchangeably in the present document.

"Moisture containing cleansing articles", "wipes", "wiping articles" are products generally comprising a substrate and a lotion. The substrate can be a nonwoven material comprising synthetic polymer fibers (such as from thermoplastic polymers), include natural fibers such as cellulosic fibers, or comprise a mixture of both. Moisture containing cleansing articles can have personal hygiene uses (such as baby wipes), cosmetic uses (make-up removal wipes, cleansing wipes, etc.) or other more general uses (for other human body parts, for animals or plants, or for delicate objects or surfaces). Examples and illustrations in this document will focus on baby wipes, without limiting the invention to the other uses.

"Lotions", or "softening lotions or compositions", are a substantially liquid mixture of compounds that impregnate the moisture containing cleansing article. The lotion is, in most instances, intended to help the removal of residues (such as feces, urine and perspiration), to hydrate the treated surface (e.g., facial or perianal skin), to soften the treated surfaces, or to protect the treated surfaces by leaving a light coating of lotion compounds on the treated surfaces after the treatment. In many instances, the lotions are mixtures of hydrophilic compounds, water and oily compounds (such as silicon-based lotions, silicon polyether containing lotions, micro emulsions). The lotions can include emulsifiers to form, for example, emulsions.

"Visual pH indicators", "pH strip", "pH sticks" are articles or chemicals that change color in response to the pH of their environment (for example when contacted with an aqueous solution). Generally the color change is the result of a change in the structure of a pH sensitive chemical (e.g., an indicator dye). The chemical is bound to a substrate such as a paper or a synthetic substrate, for easy handling.

"pH buffer(s)", "buffering system", "buffering salts", "buffer(s)" or "pH buffering salts" are chemicals that have the ability to buffer the pH change of their environment when put in solution. A buffer is a substance which by its presence in solution increases the amount of acid or alkali that must be added to cause unit change in pH. The salts can be in a solid form for example crystalline form or precipitated powder or can be dissolved in a solution. Buffers for this invention can comprise organic or/and inorganic species or mixture thereof. Examples of relevant buffers comprise: phosphoric acid, and its salts, ammonia and its salts, sulfuric acid and its salts, carboxylic acid and it's salts, carbonic acid and it's salts, citric acid and its salts, acetic acid and its salts, tartric acid and its salts, boric acid and its salts, phtalic acid and its salts or organic buffering systems such as TRIS-(hydroxymethyl aminomethane), triethanolamine, 2,4,6 trimethylpyridine, glycin, glycylglycin, diethanolamine, piperazin-1,4-bis(2-ethansulfonicacid), imidazdol. Buffers exhibit best buffering effects at a pH around their intrinsic pKa. General information on buffers can be found in chemistry textbooks, in particular "Chemistry ("Chemie")", Dr Hans Rudolf Christen, 1977, Press Diesterweg-Sauerländer, ISBN: 3-7941-0169-1".

The invention describes a system comprising a visual pH indicator and a moisture containing cleansing article, a process and the use of such a system. One use of the system of the present invention can be to compare the ability of different moisture containing cleansing articles to restore healthy, natural, substantially neutral skin conditions. The system can be used as a demonstration kit in which the consumer can perform the test by using the components provided with the system, and by following instructions provided with the system. The kit can be distributed, mailed to consumers or can be inserted into magazines or publications. The system or the corresponding demonstration kit can be useful to highlight differences between moisture containing cleansing articles (and their lotions) in sale events.

In some embodiments the elements of the system (such as the pH indicator, the moisture containing cleansing article(s)) are juxtaposed, that is provided in close relation to each other for easier use: For example the pH indicator, with or without the pH buffer, can be glued or attached by any means to the pack containing the moisture containing cleansing article(s) or to the moisture containing cleansing article(s) itself. In other embodiments, the elements are packed separately but can be easily unpacked by the person handling the system. In further embodiments the elements of the system are presented in a box, carton, pouch, leaflet, printed document or magazine. Alternatively some elements of the system, such as the visual pH indicator and/or the buffering salts can be integral parts of the presenting support or pack (for example can be printed directly on the leaflets, magazine, box or printed document), or being integral part of the wipe.

The system allows for an easy, convenient evaluation of some key characteristics of moisture containing cleansing article lotion. The pH of the lotion can be easily and quickly revealed by the visual pH indicator, that changes color if the pH of the lotion is about a defined threshold. The threshold is selected to correspond to the pH range close to the one of the skin, namely a pH of 4.0, 5.0, or 5.5. Alternatively the threshold value can be 8.0, 7.0 6.5, 6.0. Visual pH indicators (including those in a form of paper strip or sticks) that are active over the specified ranges are well known and easily commercially available from many chemical companies, such as Merck Co (Germany).

It has been found that the system of the present invention can comprise pH buffers. When the lotion is put in contact with the buffer, the lotion equilibrates with the buffer in an acid ⇔ base equilibrium. The final pH of the lotion after equilibration (as measured by the visual pH indicator of the system) is therefore the result of the interaction of the lotion with the buffer (the pH indicator is assumed to bring negligible buffering capacity to the system. The buffering capacity of the pH indicator has nevertheless to be counted as part of the total buffering capacity of the buffer in the system). As such the system exhibits an "inertia" in the measurement of the pH of the lotion. That "inertia" is provided by the buffering capacity of the buffer. The buffer (i.e., its buffering capacity) is intended to correspond to the buffering capacity of the residues (of feces, urine, perspiration, make-up—for instance). In that respect, the measurement of the pH of the lotion in presence of the buffer (as illustrated by the present invention), corresponds to the measurement of the pH of the lotion and skin after the wiping action and after the lotion has somewhat interacted with the feces residues. In other words, the system enables the illustration of the pH of the baby skin after the wiping action. As such, the system allows for a unique comparison of the capacity of moisture containing cleansing articles to restore natural skin conditions.

The association of a buffer with the system presented hereby characterizes one of the findings of this invention, as a unique way to measure not only the pH of a lotion, but also its buffering capacity.

It has been found that the invention—in some of its embodiments—performs best when the pH buffer has a pKa value equal to or greater than the pH of the color change of the visual pH indicator. Additionally, in some other embodiments, the pH of the color change of the visual pH indicator is equal to or greater than the pH of the lotion.

Many of the residues usually removed by the wiping action often tend to render their environment alkaline over time (for example residues of feces or urine). The buffer can therefore also provide for an alkaline pH in the system. In some embodiments, the pKa of the buffer (when put in solution) is at least 5.5, alternatively at least 7.5, 8.0, 8.5, 9.5, 10, 11, and 12.

In some embodiments, the visual pH indicator and/or the buffer are provided in a solid form (such as crystals, precipitated and/or dried powders). These chemicals can be made in the form of pellets or compacted powders. These chemicals can also be coated or deposited on a substrate such as a paper strip or a synthetic stick, for easier handling and convenience, either separately or as a mixture. In one embodiment, the visual pH indicator and the buffer have both been deposited or absorbed as solid chemicals at the surface of a strip of paper or of synthetic polymer. Examples of suitable visual pH indicators are: phenolphtaleine, tetrabromophenolphtaleine, m-cresolpurpur, bromcresolpurpur, thymolblue, phenylred, bromthymolblue, methyl red, thymoiblue, Bromcresol green, Bromcresol purple, chlorphenol red, Bromphenol blue, p-Nitrophenol, Azolitmin, Phenol red, Neutral red, Rosolic acid, Cresol red, alpha-Naphtholphthalein, Tropeolin OOO, Thymol blue, Phenoiplithalein, alpha-Naphtholbenzein, Thymolphthalein, Nile blue, Alizarin yellow, nitrazin yellow, brilliant yellow, Salicyl yellow, Diazo violet, Tropeolin O, Nitramine, Poirrier's blue, Trinitrobenzoic acid, or mixtures thereof.

Alternatively the visual pH indicator and/or the buffer are provided in a liquid form, either as separately or as a mixture.

In other alternatives, the pH indicators and/or the pH buffer are first made as liquid solution(s), absorbed or deposited on a substrate (such as a strip of absorbing or not absorbing substrates, for example as a strip of paper), and then dried. The buffer and/or the pH visual indicator can be released from the substrate by dissolving the dried chemicals in a solution (for example water). The solution is then used as part of the system of the present invention. Alternatively. the dried chemicals are dissolved directly in the wipe lotion.

A buffer solution comprises at least 2 species of the buffer in solution: A first specie is capable of reacting with $OH^-$ and the second specie is capable of reacting with $H_3O^+$. The two species must not react with each other. Many buffers are prepared by combining a weak acid and its conjugate (acetic acid and sodium acetate) or a weak base and its conjugate (ammonia and ammonium chloride). In general, the pH range in which a buffer solution is effective is +/− one pH unit on either side of the pKa. The Henderson-Hasselbalch equation provides the information needed to prepare a buffer.

$$pH = pKa + \log\frac{[conjugate base]}{[weak acid]}$$

There is a limit to the amount of acid or base that can be added to a buffer solution before one of the components is used up. This limit is called the buffer capacity and is defined as the moles of acid or base necessary to change the pH of one liter of solution by one unit.

$$\text{Buffer Capacity} = \frac{(\text{number of moles of } OH^- \text{ or } H_3O^+ \text{ added})}{(\text{pH change})(\text{volume of buffer in } L)}$$

The pH buffer of the invention can be an organic or inorganic buffer, or a mixture thereof, and can include one of more species, alone or in combinations, from the list: phosphoric acid and its salts, ammonia and its salts, sulfuric acid and its salts, carboxylic acid and its salts, citric acid and its salts, acetic acid and its salts, tartric acid and its salts, boric acid and its salts, phtalic acid and its salts, carbonic acid and its salts, bicarbonate salts, TRIS-(hydroxymethyl aminomethane) triethanolamine, 2,4,6 trimethylpyridine, glycin, glycylglycin, diethanolamine, piperazin-1,4-bis(2-ethansulfonicacid), imidazol.

The pH buffer of the present invention can have a buffering capacity of adding at least 0.0001 mol/l of an acid or base without changing the pH value by 1 pH unit or more. Alternatively, the buffering capacity can be 0.001, 0.01, 0.1, 1 or 10 mol/l.

In some embodiments, user instructions are provided as part of the system of the present invention. Typically the instructions are written instructions, but can also be provided as audio, video, visual graphics or combination thereof. The instructions can provide information to the user on the importance of the skin health, on the alteration of skin induced over time by residues, on the benefits of lotions for wipes and/or the benefits of a natural pH balance. The instructions can indicate to the user how to use the components of the system of the invention to evaluate wipes. For example, the instructions can describe the steps of contacting a wipe with a visual pH indicator in presence of a buffer. The instructions can describe that 1, 2, 3, 5, 7, 9, 10 or more prolonged contacts of about 0.5 second are needed to best visualize the results. Alternatively or additionally, the instructions can describe the dissolution of a solid form of pH buffer and pH indicator absorbed on a substrate(s) into water (or into an aqueous solution). Alternatively or additionally, the instructions can include the use of the resulting solution for contacting the wipe and evaluating their pH and/or buffering capacity. The instructions can describe the steps of reading the pH color of the visual pH indicator and/or comparing the color with a reference. The reference can be provided in a written form, as graphics, as audio, as video, as icons, as colors or any combination thereof, or in any other suitable means. The instructions can include information to evaluate moisture containing cleansing articles as for the pH of the wipe lotion, the pH of the skin after use and/or buffering capacity of the wipe lotion.

Example: In one embodiment of the present invention the pH indicator is "Brilliant Yellow" available from Merck (Germany), the pH buffer is a TRIS-(hydroxymethyl aminomethane). The pH indicator and pH buffer have been both coated onto a substrate (a stripe of synthetic material of 5 cm long×5 mm wide). The moisture containing cleansing articles are PAMPERS Baby Wipes Sensitive, as sold in Germany at the filing date of the present application. Other wipes have been tested, including JOHNSON & JOHNSON ExtraCare Aloe & Willow herb, NIVEA Baby Sensitive, HUGGIES Cotton Touch Sensitive/Ziplock, and AUCHAN Prestige Sensitive as illustrated in table 1.

The measurement of the pH of the lotion is made according to any method known in the art (for example, extraction and collection of the lotion from the wipe by application of a load on the stack of wipes, collection of the lotion and pH measurement of the collected lotion via an electronic pH-meter.

The protocol for the testing reported in table 1 is as follows: The wipe is removed from its packaging and contacted 5 times (each for about 0.5 to 1 second) under light hand pressure to the substrate (strip) coated with the pH indicator and the buffer (in this case a TRIS buffer). The change of color of the strip is evaluated by comparison to a reference colored chart. One observes that PAMPERS Baby Wipes Sensitive induces a change of color of the pH visual indicator from orange/red to yellow. The other wipes tested don't induce a color change to yellow. The change of color to yellow indicates a final pH of below 7.0. The results are interpreted as a better ability of the PAMPERS Baby Wipes Sensitive wipes to restore a neutral pH on the skin, even in presence of the "reservoir" of alkalinity provided in-situ by the feces residues and in the experiment by the pH buffer of the system of the invention.

TABLE 1

| Wipe product | Pampers Sensitive wipes | J & J ExtraCare Aloe & Willowherb | Nivea Baby Sensitive | Huggies Cotton Touch Sensitive/ Ziplock | Auchan Prestige Sensitive |
|---|---|---|---|---|---|
| Labeled ingredients | Aqua, Dimethicone, Propylene Glycol, Aloe Barbadensis, Bisabolol, Chamomilla Recutita, Sodium Acrylates, Vinyl Isodecanoate Crosspolymer, Sorbitan Oleate, Caprylic/Capric Triglyceride, Sodium Phosphate, Sodium Bonzoate, Methylparaben, Ethylparaben, Propylparaben, Disodium EDTA, Polysorbate 20 | Aqua, Paraffinum Liquidum, Ceteareth-12, Phenoxyethanol, Glyceryl Stearate, Glyceryl Oleate, Aloe Barbadensis Leaf Juice, *Epilobium Angustifolium* Extract, *Avena Sativa*, Propylene Glycol, Coco-Glucoside, Ceteareth-20, Cetearyl Alcohol, Cetyl Palmitate, Tetrasodium EDTA, Cetylpyridinium Chloride, Citric Acid, Lactic Acid, Sodium Benzoate, Potassium Sorbate, PEG-4 Laurate, Iodopropynyl Butylcarbamate, Parfum | Aqua, PEG-40 Hydrogenated Castor Oil, Glycerin, Phenoxyethanol, Methylparaben, Potassium Sorbate, Sodium Citrate, Panthenol, Citric Acid, Propylparaben | Aqua, Potassium Laureth Phosphate, Glycerin, Polysorbate 20, Tetrasodium EDTA, DMDM Hydantoin, Methylparaben, Malic acid | Aqua, Paraffinum liquidium, Glycerin, Caprylyl/Capryl, Glucoside, Butylene Glycol, Sodium Polyacrylate & Ethylhexylstearate & Trideceth 6, Prunus Amygdalus (Sweet Almond) Oil, Propylene Glycol & Mel Extract, Methylparaben, Allantoin, 2-Bromo-2-Nitropropane-1.3 Diol, Butylparaben, Ethylparaben, Propylparaben. |
| Lotion pH (measured) | 5.4 | 5.4 | 5.3 | 5.6 | 6.1 |
| Buffering capacity of the lotion (measured as the volume of NaOH added to reach a final pH of 7.0 (titration curve) | 13.0 ml | 1.9 ml | 4.6 ml | 6.1 | 7.0 ml |
| Color of the visual pH indicator after contacting the wipe of the pH color indicator in presence of a pH buffer (Tris) | Yellow | red | dark-orange | light-orange | Red |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A test kit for measuring and quantifying the capacity of moisture containing cleansing article to neutralize alkalinity of residues on human skin and to restore natural pH of skin, by evaluating the pH and buffering potential of said moisture containing cleansing article, comprising:
   a moisture containing cleansing article comprising a fibrous substrate and a lotion disposed on said fibrous substrate;
   a substrate for simulating human skin with said alkaline residues comprising a visual pH indicator and a pH buffer for providing the reservoir of alkalinity disposed on said substrate, wherein the pH buffer is adapted to modify the ability of said lotion to maintain pH of natural human skin by shifting its acid-base equilibrium to simulate interaction of said lotion with said alkaline residue, and further wherein said visual pH indicator changes color at a pH above 4.0, and is adapted to indicate the final pH of said lotion that interacted with the pH buffer.

2. The test kit according to claim 1, wherein the pH buffer has a pKa value equal to or greater than the pH of the color change of the visual pH indicator, and further wherein the pH of the color change of the visual pH indicator is equal to or more basic than the pH of the lotion.

3. The test kit according to claim 2, wherein the pH buffer has a pKa value of at least 5.5.

4. The test kit according to claim 2, wherein the pH buffer has a pKa value of at least 7.0.

5. The test kit according to claim 1, wherein the pH buffer and the visual pH indicator are both in a solid form.

6. The test kit according to claim 1, wherein the visual pH indicator or the pH buffer is in a liquid aqueous form.

7. The test kit according to claim 1, wherein the visual pH indicator and the pH buffer are present in the liquid aqueous form.

8. The test kit according to claim 1, wherein said substrate comprising the visual pH indicator and the pH buffer is physically juxtaposed to the moisture containing cleansing article.

9. The test kit according to claim 1, wherein the pH buffer has a buffering capacity of at least adding 0.0001 mol/l of an acid or base without changing the pH value by 1 pH unit or more.

10. The test kit according to claim 1, wherein the pH buffer is selected from the group consisting of inorganic buffers, organic buffers and mixtures thereof.

11. The test kit according to claim 10, wherein the pH buffer is selected from the group consisting of phosphoric acid and its salts, ammonia and its salts, sulfuric acid and its salts, carboxylic acid and its salts, citric acid and its salts, acetic acid and its salts, tatric acid and its salts, boric acid and its salts, phtalic acid and its salts, carbonic acid and its salts, bicarbonate, TRIS-(hydroxymethyl aminomethane), triethanolamine, 2,4,6 trimethylpyridine, glycin, glycylglycin, diethanolamine, piperazin-1,4-bis(2-ethansulfonicacid), and imidazol.

12. The test kit according to claim 1, wherein the visual pH indicator changes color at a pH above 5.0.

13. The test kit according to claim 1, wherein the test kit comprises a pack of single or multiple moisture containing cleansing articles.

14. The test kit according to claim 1, wherein the test kit further comprises a set of instructions.

* * * * *

UNITED STATES PATENT AND TRADEMARK OFFICE
CERTIFICATE OF CORRECTION

| | | |
|---|---|---|
| PATENT NO. | : 7,727,468 B2 | Page 1 of 1 |
| APPLICATION NO. | : 11/153751 | |
| DATED | : June 1, 2010 | |
| INVENTOR(S) | : Herrlein et al. | |

It is certified that error appears in the above-identified patent and that said Letters Patent is hereby corrected as shown below:

<u>Column 5</u>

Line 11, delete "thymoiblue" and insert --thymolblue--.

Line 12, delete "chiorphenol" and insert --chlorphenal--.

Line 15, delete "Phenoiplithalein" and insert --Phenolphtalein--.

Line 28, after the word alternatively delete the ".".

Signed and Sealed this
Twelfth Day of April, 2011

David J. Kappos
*Director of the United States Patent and Trademark Office*